United States Patent
Almiñana Domenech et al.

(10) Patent No.: US 9,393,186 B2
(45) Date of Patent: Jul. 19, 2016

(54) SYNTHETIC PEPTIDES USEFUL IN THE TREATMENT OF THE SKIN AND USE THEREOF IN COSMETIC OR DERMOPHARMACEUTICAL COMPOSITIONS

(75) Inventors: Nuria Almiñana Domenech, Barcelona (ES); Wim Van Nest, Barcelona (ES); Cristina Carreño Seraima, Barcelona (ES); Joan Cebrian Puche, Barcelona (ES); Elena Passerini, Sant Cugat del Vallès (ES); Arturo Puig Montiel, Barcelona (ES)

(73) Assignee: Lipotec, S.A., Gava, Barcelona (ES)

( * ) Notice: Subject to any disclaimer, the term of this patent is extended or adjusted under 35 U.S.C. 154(b) by 1543 days.

(21) Appl. No.: 12/295,554

(22) PCT Filed: Mar. 30, 2007
(Under 37 CFR 1.47)

(86) PCT No.: PCT/ES2007/000180
§ 371 (c)(1),
(2), (4) Date: Dec. 13, 2010

(87) PCT Pub. No.: WO2007/113356
PCT Pub. Date: Oct. 11, 2007

(65) Prior Publication Data
US 2013/0309281 A1    Nov. 21, 2013

(30) Foreign Application Priority Data

Mar. 31, 2006 (ES) .................................. 200600846

(51) Int. Cl.
| | | |
|---|---|---|
| A61K 8/64 | (2006.01) | |
| A61Q 19/00 | (2006.01) | |
| A61Q 19/08 | (2006.01) | |
| C07K 5/10 | (2006.01) | |
| C07K 5/00 | (2006.01) | |
| C07K 5/11 | (2006.01) | |

(52) U.S. Cl.
CPC . *A61K 8/64* (2013.01); *A61Q 19/00* (2013.01); *A61Q 19/08* (2013.01); *C07K 5/1019* (2013.01); *A61K 2800/522* (2013.01)

(58) Field of Classification Search
CPC ............. A61K 8/64; A61K 8/30; A61K 8/18; A61K 2800/40; A61K 2800/00; A61Q 19/08; A61Q 19/00; C07K 5/1019; C07K 5/10; C07K 5/04; C07K 5/00
See application file for complete search history.

(56) References Cited

U.S. PATENT DOCUMENTS

| | | |
|---|---|---|
| 5,510,328 A | 4/1996 | Polarek et al. |
| 6,042,841 A | 3/2000 | Alaluf et al. |
| 6,287,553 B1 | 9/2001 | Alaluf et al. |
| 6,423,325 B1 | 7/2002 | Alaluf et al. |
| 6,440,434 B1 | 8/2002 | Barrett et al. |
| 6,455,057 B1 | 9/2002 | Barrett et al. |
| 6,509,314 B1 | 1/2003 | Ruoslahti et al. |

(Continued)

FOREIGN PATENT DOCUMENTS

| | | |
|---|---|---|
| FR | 2834462 | 7/2003 |
| JP | 2004051508 | 2/2004 |

(Continued)

OTHER PUBLICATIONS

Wiberg et al., "Complexes of matrilin-1 and biglycan or decorin connect collagen VI microfibrils to both collagen II and aggrecan" J. Biol. Chem. 278, pp. 37698-37704 (2003).

(Continued)

*Primary Examiner* — Karlheinz R Skowronek
*Assistant Examiner* — Catherine Mader
(74) *Attorney, Agent, or Firm* — Fay Sharpe LLP

(57) ABSTRACT

The present invention relates to peptides of general formula (I) capable of regulating fibrillogenesis, stereoisomers thereof and mixtures thereof, which may or may not be racemic, and the cosmetically or dermopharmaceutically acceptable salts thereof, wherein Z is alanyl, allo-isoleucyl, glycyl, isoleucyl, isoseryl, isovalyl, leucyl, norleucyl, norvalyl, prolyl, seryl, threonyl, allo-threonyl or valyl; n and m may vary between 1 and 5; AA is selected from the group consisting of natural amino acids encoded in their L- or D-form and non-encoded amino acids; x and y may vary between 0 and 2; $R_1$ is H or alkyl, aryl, aralkyl or acyl group; and $R_2$ is amino, hydroxyl or thiol, all of them substituted or non-substituted with aliphatic or cyclic groups. A method for obtaining cosmetic or dermopharmaceutical compositions containing them and use thereof for treating the skin, preferably those skin conditions which require regulating fibrillogenesis, such as aging and/or the softening of the appearance of scars.

(I)

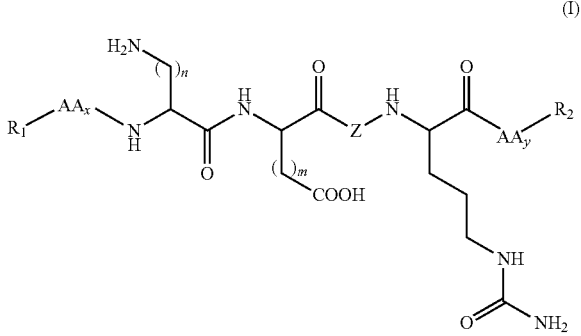

23 Claims, No Drawings

(56) References Cited

U.S. PATENT DOCUMENTS 6,551,602 B1     4/2003    Barrett et al.
2003/0124152 A1   7/2003    Pang

FOREIGN PATENT DOCUMENTS

WO    WO 02/036091      5/2002
WO    WO 2006/008392   * 1/2006          A61K 7/48

OTHER PUBLICATIONS

Aumailley, et al. "Structure and biological activity of the extracellular matrix" J. Mol. Med. 76, pp. 253-265 (1998).
Culav, et al. "Connective tissues: matrix composition and its relevance to physical therapy" Phys. Ther. 79, pp. 308-319 (1999).
Scott "Elasticity in extracellular matrix 'shape modules' of tendon, cartilage, etc. A sliding proteoglycan-filament model" J. Physiol. 553, pp. 335-343(2003).
Ameye, et al., "Mice deficient in small leucine-rich proteoglycans: novel in vivo models for osteoporosis, osteoarthritis, Ehlers-Danlos syndrome, muscular dystrophy and corneal diseases" Glycobiology 12, pp. 107R-116R (2002).
Perrimon, et al.,"Cellular functions of proteoglycans- an overview" Semin. Cell Dev. Biol.12, pp. 65-67 (2001).
Iozzo, "Matrix proteoglycans: from molecular design to cellular function" Annu. Rev. Biochem. 67, pp. 609-652 (1998).
Ruoslahti, "Proteoglycans in cell regulation" J. Biol. Chem. 264, No. 23, pp. 13369- 13372 (1989).
Sugahara, "Recent advances in the study of the biosynthesis and functions of sulfated glycosaminoglycans" Curr. Opin. Struct. Biol. 10, pp. 518-527(2000).
Zamfir, "Structural investigation of chondroitin/dermatan sulfated oligosaccharides from human skin fibroblast decorin" Glycobiology 13, pp. 733-742 (2003).
Iozzo, et al. "The family of the small leucine-rich proteoglycans: key regulators of matrix assembly and cellular growth" Crit. Rev. Biochem. Mol. Biol. 32, 141-174(1997).
Ramamurthy, et al., "Recombinant decorin glycoforms. Purification and structure" J. Biol. Chem. 271, 19578-19584 (1996).
Bianco, et al., "Expression and localization of the two small proteoglycans biglycan and decorin in developing human skeletal and non-skeletal tissues" J. Histochem. Cytochem. 38, 1549-1563 (1990).
Zimmermann, et al., "Versican is expressed in the proliferating zone in the epidermis and in association with the elastic network of the dermis" J. Cell Biol. 124, pp. 817-825 (1994).
Carrino, et al., "Age-related changes in the proteoglycans of human skin" Arch. Biochem. Biophys. 373, pp. 91-101 (2000).
Danielson, et al., "The human decorin gene: intron-exon organization, discovery of two alternatively spliced exons in the 5' untranslated region, and mapping of the gene to chromosome 12q23" Genomics 15, pp. 146-160 (1993).
Svensson, et al., "Decorin-binding sites for collagen type I are mainly located in leucine-rich repeats 4-5" J. Biol. Chem. 270, pp. 20712-20716 (1995).
Keene, et al., "Type Vi microfilaments interact with a specific region of banded collagen fibrils in skin" J. Histochem. Cytochem. 46, pp. 215-220 (1998).
Kresse, et al., "Critical role of glutamate in a central leucine-rich repeat of decorin for interaction with type I collagen" J. Biol. Chem. 272, pp. 18404-18410 (1997).
Tenni, et al., "Interaction of decorin with CNBr peptides from collagens I and II. Evidence for multiple binding sites and essential lysyl residues in collagen" Eur. J. Biochem. 269, pp. 1428-1437 (2002).
Scott, "Proteodermatan and proteokeratan sulfate (decorin, lumican/fibromodulin) proteins are horseshoe shaped. Implications for their interactions with collagen" Biochemistry 35, pp. 8795-8799 (1996).
Danielson, et al., "Targeted disruption of decorin leads to abnormal collagen fibril morphology and skin fragility" J. Cell. Biol. 136, pp. 729-743 (1997).
Dombi, et al., "Correlation of high-speed tensile strength with collagen content in control and lathyritic rat skin" J. Surg. Res. 54, pp. 21-28 (1993).
Schaefer, et al., "Absence of decorin adversely influences tubulointerstitial fibrosis of the obstructed kidney by enhanced apoptosis and increased inflammatory reaction" Am. J. Pathol. 160, pp. 1181-1191 (2002).
Iozzo, "The biology of the small leucine-rich proteoglycans" J. Biol. Chem. 274, pp. 18843-18846 (1999).
Schonherr, et al., "Decorin core protein fragment Leu155-Va1260 interacts with Tgf-beta but does not compete for decorin binding to type I collagen" Arch. Biochem. Biophys. 355, pp. 241-248 (1998).
Hunzelmann, et al., "Transforming growth factor-beta reverses deficient expression of type (I) collagen in cultured fibroblasts of a patient with metageria" Biochim. Biophys. Acta. 1360, pp. 64-70(1997).
Oikarinen, "The aging of the skin: chronoaging versus photoaging" Photodermatol. Photoimmunol. Photomed. 7, pp. 3-4 (1990).
Bernstein, et al., "Differential expression of the versican and decorin genes in photoaged and sun-protected skin. Comparison by immunohistochemical and northern analyses" Lab. Invest. 72, pp. 662-669 (1995).
Scott, et al., "Fibroblasts from post-burn hypertrophic scar tissue synthesize less decorin than normal dermal fibroblasts" Clin. Sci. (Lond). 94, pp. 541-547 (1998).
Garg, et al., "Purification and characterization of iduronic acid-rich and glucuronic acid-rich proteoglycans implicated in human post-burn keloid scar" Carbohydr. Res. 207, pp. 295-305 (1990).
Carrino, et al., "Age related changes in the proteoglycans of human skin" J. Biol. Chem. 278, pp. 17566-17572 (2003).
Bhide, et al., "Collagen phagocytosis by fibroblasts is regulated by decorin" J. Biol. Chem. 280, pp. 23103-23113 (2005).
Scott, "Proteodermatan and proteokeratan sulfate (decorin, lumican/fibromodulin) proteins are horseshoe shaped. Implications for their interactions with collagen" Biochemistry 35, pp. 8795-8799(1996).
Roberts, et al., "Unusual amino acids in peptide synthesis" the Peptides, vol. 5, Chapter VI, pp. 341-448 Gross E. And Meienhofer J., Eds., Academic Press, New York, USA (1983).
Stewart, et al., "Solid Phase Peptide Synthesis, 2nd edition", Pierce Chemical Company, Rockford, Illinois, pp. 1-9 and 71-95 (1984).
Bodansky, et al., "The practice of Peptide Synthesis," Springer Verlag, New York pp. 77126 (1984).
Lloyd-Williams, et al., "Chemical Approaches to the Synthesis of Peptides and Proteins," CRC, Boca Raton, FL, USA, pp. 19-93 (1997).
Kullmann, "Proteases as catalysts for enzymic syntheses of opioid peptides," J.Biol.Chem. 255 pp. 8234-8238 (1980).
Atherton, et al., "Solid Phase Peptide Synthesis: a practical approach," IRL Oxford University Press, pp. 1-61 (1989).
Matsueda et al, "A p-methylbenzhydrylamine resin for improved solid-phase synthesis of peptide amides," Peptides 2, pp. 45-50 (1981).
Barlos et al., "Darstellung geschützter Peptid-Fragmente unter Einsatz substituierter Triphenylmethyl-Harze," Tetrahedron Lett., 30, pp. 3943-3946 (English Summary only), (1989).
Barlos et al., "Veresterung von partiell geschützten Peptid-Fragmenten mit Harzen. Einsatz von 2-Chlorotritylchlorid zur Synthese von Leu1-Gastrin I," Tetrahedron Lett., 30, pp. 3947-3951 (English Summary only) (1989).
Albericio, et al., "Preparation and application of the 5-(4-(9-fluorenylmethyloxycarbonyl) aminomethyl-3,5-dimethoxyphenoxy)valeric acid (PAL) handle for the solid-phase synthesis of C-terminal peptide amides under mild conditions," J. Org. Chem., 55 pp. 3730-3743 (1990).
Rink, "Solid-phase synthesis of protected peptide fragments using a trialkoxy-diphenyl-methylester resin," Tetrahedron Lett., 28 pp. 3787-3790 (1987).
Wang, "p-Alkoxybenzyl Alcohol Resin and p-Alkoxybenzyloxycarbonylhydrazide Resin for Solid Phase Synthesis of Protected Peptide Fragments," J.Am.Chem.Soc., 95, pp. 1328-1333 (1973).

(56) References Cited

OTHER PUBLICATIONS

Schaab, "Impregnating Fabrics With Microcapsules," HAPPI May, pp. 84-86 (1986).
Nelson, "Application of microencapsulation in textiles," Int. J. Pharm., 242 pp. 55-62.
Kaiser, et al., "Color Test for Detection of Free Terminal Amino Groups in the Solid-Phase Synthesis of Peptides," pp. 595-598 (1970).
IUPAC IUB Commission of Biochemical Nomenclature specified in Eur. J. Biochem. 138:9 p. 9-37 (1984).
Stander, et al., "Transforming growth factor-β and p-21: multiple molecular targets of decorin-mediated suppression of neoplastic growth," Cell Tissue Res, 296, pp. 221-227 (1999).
Carrino, et al. "Age-related changes in the proteoglycans of human skin," Arch. Biochem. Biophys. vol. 373, pp. 91-101(2000).
Honda, et al., "The proteoglycans in hypertrophic scar" J. Dermatol. vol. 13, pp. 326-333 (1986).

* cited by examiner

SYNTHETIC PEPTIDES USEFUL IN THE TREATMENT OF THE SKIN AND USE THEREOF IN COSMETIC OR DERMOPHARMACEUTICAL COMPOSITIONS

This application is a National Stage Application of PCT/ES2007/000180, filed 30 Mar. 2007, which claims benefit of Serial No. P200600846, filed 31 Mar. 2006 in Spain and which applications are incorporated herein by reference. To the extent appropriate, a claim of priority is made in each of the above disclosed applications.

FIELD OF THE INVENTION

The present invention relates to synthetic peptides regulating fibrillogenesis and to cosmetic or dermopharmaceutical compositions containing said peptides useful in the treatment of the skin, preferably for treating those skin conditions requiring a regulation of fibrillogenesis such as the treatment of aged skin (either intrinsic aging due to the passage of time and to genetic factors or extrinsic aging due to prolonged exposure to the sun and/or to environmental contaminants such as ultraviolet (UV) radiation from sunlight, chemical contaminants, cigarette smoke and pollution), or as coadjuvants in healing processes to soften the appearance of scars.

BACKGROUND OF THE INVENTION

The skin is formed by two layers: the epidermis and the dermis. The outermost layer is the epidermis, which is mostly formed by keratinocytes, melanocytes and Langerhans' cells, and its basic function is to retain the water of the body, act as a barrier mechanism against harmful chemical agents as well as against pathogenic organisms and carry out cell renewal processes. The innermost layer, the dermis, formed by fibroblasts, adipocytes and macrophages, is strongly bound to the epidermis through the basement membrane and contains a number of nerve endings providing the touch and temperature sensations. It also houses hair follicles, sweat glands, sebaceous glands, apocrine glands and blood vessels, and one of its main functions is to maintain the elasticity and appearance of the skin.

The dermis also includes the extracellular matrix, formed by a set of extracellular proteins (fibrous proteins, glycoproteins and proteoglycans) the key function of which is to maintain the structure of the skin and the correct functioning and development of the tissues depends on their formation and regulation being correct [Wiberg C., Klatt A. R., Wagener R., Paulsson M., Bateman J. F., Heinegard D. and Morgelin M. (2003) "*Complexes of matrilin-1 and biglycan or decorin connect collagen VI microfibrils to both collagen II and aggrecan*" *J. Biol. Chem.* 278, 37698-37704]. The two most important fibrous proteins of the extracellular matrix are collagen and elastin, responsible for the mechanical properties of tissues, such as the capacity to resist stress, compression, extensibility and torsion. Proteglycans have a structural and metabolic function, whereas glycoproteins, together with proteoglycans, serve as connecting bridges between the components of the matrix and the cells [Aumailley M. and Gayraud B. (1998) "*Structure and biological activity of the extracellular matrix*" *J. Mol. Med.* 76, 253-265; Culav E. M., Clark C. H. and Merrilees M. J. (1999) "*Connective tissues: matrix composition and its relevance to physical therapy*" *Phys. Ther.* 79, 308-319; Scott J. E. (2003) "*Elasticity in extracellular matrix 'shape modules' of tendon, cartilage, etc. A sliding proteoglycan-filament model*" *J. Physiol.* 553, 335-343].

Collagen

Collagens are a family of fibrous proteins of the extracellular matrix which form 25% of the total protein mass in mammals. They have been classified into more than 20 families, all of them with individual characteristics fulfilling specific functions in different tissues.

The main characteristic of collagen is its helical structure formed by the association of three polypeptide chains rich in glycine and proline. Alterations in its amino acid composition cause a dysfunction and loss of its mechanical properties [Culav E. M., Clark C. H. and Merrilees M. J. (1999) "*Connective tissues: matrix composition and its relevance to physical therapy*" *Phys. Ther.* 79, 308-319]. These polypeptide chains can be associated to one another forming fibrils having a diameter of 10-300 nm and a length of up to several hundreds of micrometers in mature tissues. These fibrils often aggregate in larger structures, such as bundles of cables, which can be seen by electron microscopy as collagen fibers with a diameter of several micrometers. This process is known as [Aumailley M. and Gayraud B. (1998) "*Structure and biological activity of the extracellular matrix*" *J. Mol. Med.* 76, 253-265]. Not all collagens have the capacity to form fibrils; only type I, II, III, V and XI collagens, which are known as fibrillar collagens.

The dermis of an adult is basically formed by type I (80-90%), III, and V fibrillar collagens. Type I collagen fibers generally have a larger diameter, a characteristic which is correlated with their capacity to support a larger mechanical load. Type II collagen plays a role in the extensibility of tissue, and over the years it is replaced by type I collagen molecules, a process which is partially responsible for mature skin being less extensible than childhood skin. Type V collagen is associated to those of type I and III by regulating the diameter of fibrils ["*The Biology of the Skin*", Freinkel R. K. and Woodley D. T., eds. The Parthenon Publishing Group, 2001; Culav E. M., Clark C. H. and Merrilees M. J. (1999) "*Connective tissues: matrix composition and its relevance to physical therapy*" *Phys. Ther.* 79, 308-319].

The mutations in the collagen molecule or in the molecules involved in collagen fibrillogenesis can lead to a destructured collagen such as that found in pathologies such as the Ehlers-Danlos syndrome [Ameye L. and Young M. G. (2002) "*Mice deficient in small leucine-rich proteoglycans: novel in vivo models for osteoporosis, osteoarthritis, Ehlers-Danlos syndrome, muscular dystrophy and corneal diseases*" *Glycobiology* 12, 107R-116R]. Likewise, the prolonged exposure to UV rays can damage the architecture of collagen and cause its substitution for a less structured collagen with the subsequent thinning of the skin and formation of wrinkles, Finally, the damage to the architecture of collagen can give rise to disorganized collagen deposition during repair processes, as occurs in liver cirrhosis, pulmonary fibrosis or dermal scar formation processes. Therefore, the regulation of collagen organization can be potentially useful not only for cosmetic or dermopharmaceutical treatments but also for treating various clinical conditions.

Proteoglycans

Proteoglycans are one of the major components of the extracellular matrix and are characterized by having a protein core covalently bound to carbohydrates called glycosaminoglycans (GAGs). They are involved in many of the cell processes occurring by means of molecular interactions in the cell surface, such as cell-extracellular matrix, cell-cell and receptor-ligand interactions, since they bind avidly to proteins, and are very abundant in these regions [Perrimon N. and Bernfield M. (2001) "*Cellular functions of proteoglycans—an overview*" *Semin. Cell Dev. Biol.* 12, 65-67]. Proteoglycans act as tissue organizers, they facilitate cell growth and the maturation of specialized tissues, they play an essential role as biological filters and regulate the activity of growth factors [Iozzo R. V. (1998) "*Matrix proteoglycans: from molecular design to cellular function*" *Annu. Rev. Biochem.* 67, 609-652; Ruoslahti E. (1989) "*Proteoglycans in cell regulation*" *J. Biol. Chem.* 264, 13369-13372].

GAGs are polymers formed by disaccharide repeats, generally an acetylated amino sugar (N-acetylglucosamine or N-acetylgalactosamine) alternating with uronic acid (glucuronate or iduronate), and have a high index of sulfate groups, except hyaluronic acid. Due to their high content in acid groups, they are negatively charged and tend to attract cations such as $Na^+$ and, as they are osmotically active, they attract water and allow maintaining tissue hydration. The commonest GAGs are hyaluronic acid, chondroitin sulfate, dermatan sulfate, heparan sulfate and keratan sulfate [Sugahara K. and Kitagawa H. (2000) "*Recent advances in the study of the biosynthesis and functions of sulfated glycosaminoglycans*" *Curr. Opin. Struct. Biol.* 10, 518-527; Zamfir A., Seidler D. G., Kresse H. and Peter-Katalinic J. (2003) "*Structural investigation of chondroitin/dermatan sulfated oligosaccharides from human skin fibroblast decorin*" *Glycobiology* 13, 733-742].

One type of proteoglycans are the so-called "leucine-rich proteoglycans", which do not interact with hyaluronic acid and are involved in the structuring of extracellular matrices, in the modulation of the activity of growth factors as well as in the regulation of cell growth properties [Iozzo R. V. (1997) "*The family of the small leucine-rich proteoglycans: key regulators of matrix assembly and cellular growth*" *Crit. Rev. Biochem. Mol. Biol.* 32, 141-174]. Although the different leucine-rich proteoglycans have common structural characteristics, they are markedly different in their genetic regulation, in their expression pattern as well as in their functional interactions [Ramamurthy P., Hocking A. M. and McQuillan D. J. (1996) "*Recombinant decorin glycoforms. Purification and structure*" *J. Biol. Chem.* 271, 19578-19584].

The proteoglycans of the skin include versican, decorin, biglycan and hyaluronic acid. These molecules are located in specific areas of the skin. Decorin is thus in association with dermal fibers [Bianco P., Fisher L. W, Young M. F., Termine J. D. and Robey P. G. (1990) "*Expression and localization of the two small proteoglycans biglycan and decorin in developing human skeletal and non-skeletal tissues*" *J. Histochem. Cytochem.* 38, 1549-1563], biglycan is in differentiating keratinocytes in the epidermis and in the vascular endothelium [Bianco P., Fisher L. W., Young M. F., Termine J. D. and Robey P. G. (1990) "*Expression and localization of the two small proteoglycans biglycan and decorin in developing human skeletal and non-skeletal tissues*" *J. Histochem. Cytochem.* 38, 1549-1563] and versican is detected in the basal lamina of the epidermis and in association with the fibers of the elastic network of the dermis, as well as in sweat glands and in the hair follicle coating [Zimmermann D. R., Dours-Zimmermann M. T., Schubert M. and Bruckner-Tuderman L. (1994) "*Versican is expressed in the proliferating zone in the epidermis and in association with the elastic network of the dermis*" *J. Cell Biol.* 124, 817-825]. Other studies indicate that versican is not present in the epithelium of adult skin, but is present in the connective tissues adjacent to these areas, including the dermis and in the hair follicle coating [Carrino D. A., Sorrell J. M. and Caplan A. I. (2000) "*Age-related changes in the proteoglycans of human skin*" *Arch. Biochem. Biophys.* 373, 91-101].

Decorin

Decorin is considered to be one of the key proteoglycans in the regulation of the structuring and function of many elements of the extracellular matrix. Decorin binds to growth factors, including the transforming growth factor-beta (TGF-β), to other proteins of the extracellular matrix such as fibronectin and thrombospondin, to cell membrane receptors (decorin endocytosis receptor), and can also interfere directly on the cell cycle through the induction of p21, a potent cyclin-dependent kinase (CDK) inhibitor) [Stander M., Naumann U., Wick W. and Weller M. (1999) "*Transforming growth factor-beta and p-21: multiple molecular targets of decorin-mediated suppression of neoplastic growth*" *Cell Tissue Res.* 296, 221-227].

Many of the studies on the interaction of decorin are about the binding to type I collagen, although it is known that they also interact with other collagens such as types II, III and VI collagens. Although it is considered that the main factor affecting the formation of collagen fibrils in vivo is the actual structure of collagen, there are different molecules such as decorin which can regulate and adjust this process. Decorin delays the formation of fibrils and makes it difficult, it causes a consequent reduction in the average diameters of the fibrils and forces collagen fibers to adopt a regular spatial distribution [Danielson K. G., Fazzio A., Cohen I., Cannizzaro L. A., Eichstetter L. and Iozzo R. V. (1993) "*The human decorin gene: intron-exon organization, discovery of two alternatively spliced exons in the 5' untranslated region, and mapping of the gene to chromosome 12q23*" *Genomics* 15, 146-160]. This process is mediated by the protein core of the proteoglycan, and requires it to conserve its tertiary structure [Svensson L., Heinegard D. and Oldberg A. (1995) "*Decorin-binding sites for collagen type I are mainly located in leucine-rich repeats 4-5*" *J. Biol. Chem.* 270, 20712-20716; Keene D. R., Ridgway C. C. and Iozzo R. V. (1998) "*Type VI microfilaments interact with a specific region of banded collagen fibrils in skin*" *J. Histochem. Cytochem.* 46, 215-220]. There is evidence that the triple helix of type I collagen has a specific decorin-binding site [Keene D. R., Ridgway C. C. and Iozzo R. V. (1998) "*Type VI microfilaments interact with a specific region of banded collagen fibrils in skin*" *J. Histochem. Cytochem.* 46, 215-220] and that there are additional interactions with dermatan sulfate molecules [Kresse H., Liszio C., Schonherr E. and Fisher L. W. (1997) "*Critical role of glutamate in a central leucine-rich repeat of decorin for interaction with type I collagen*" *J. Biol. Chem.* 272, 18404-18410]. Decorin binds to two adjacent parallel collagen molecules of the fibril, aiding in stabilizing the fibril and orienting fibrillogenesis. As it is bound to the collagen fibril surface, the lateral interaction between the triple helixes of collagen becomes more difficult, since it acts as a spacer and the diameter of the fibrils decreases, thus controlling the dimensions of the fibrils, specifically the uniformity of their diameter and the regular distance between them, thus allowing it to maintain the shape of the tissue [Tenni R., Viola M., Welser F., Sini P., Giudici C., Rossi A. and Tira M. E. (2002) "*Interaction of decorin with CNBr peptides from collagens I and II. Evidence for multiple binding sites and essential lysyl residues in collagen*" *Eur. J. Biochem.* 269, 1428-1437; Scott J. E. (1996) "*Proteodermatan and proteokeratan sulfate (decorin, lumican/fibromodulin) proteins are horseshoe shaped. Implications for their interactions with collagen*" *Biochemistry* 35, 8795-8799].

The importance of these interactions of decorin with collagen has also been demonstrated in vivo by means of the transgenic mice which do not have the decorin gene and therefore do not produce decorin in their organism. These animals are viable but have a very fragile skin, with a very thin dermis, with a reduced elastic strength and reduced tensile strength, and their histopathological analysis shows that their collagen fibrils have irregular diameters along the fibrils due to uncontrolled lateral aggregations [Kresse H., Liszio C., Schonherr E. and Fisher L. W. (1997) "*Critical role of glutamate in a central leucine-rich repeat of decorin for interaction with type I collagen*" *J. Biol. Chem.* 272, 18404-18410; Danielson K. G., Baribault H., Holmes D. F., Graham H., Kadler K. E. and Iozzo R. V (1997) "*Targeted disruption of decorin leads to abnormal collagen fibril morphology and skin fragility*" *J. Cell. Biol.* 136, 729-743; Keene D. R., Ridgway C. C. and Iozzo R. V. (1998) "*Type VI microfilaments interact with a specific region of banded collagen fibrils in skin*" *J. Histochem. Cytochem.* 46, 215-220]. This observation is consistent with the widely accepted fact that the strength of the skin is directly correlated with the general organization, the content and the physical properties of the fibrillar collagen network [Dombi G. W., Haut R. C. and Sullivan W. G. (1993) "*Correlation of high-speed tensile strength with collagen content in control and lathyritic rat skin*" *J. Surg. Res.* 54, 21-28]. Furthermore, said transgenic animals also have an increased collagen degradation, which contributes to their poor skin quality [Schaefer L., Macakova K., Raslik I., Micegova M., Gröne H-J., Schönherr E., Robenek H., Echtermeyer F. G., Grässel S., Bruckner P., Schaefer R. M., Iozzo R. V. and Kresse H. (2002) "*Absence of decorin adversely influences tubulointerstitial fibrosis of the obstructed kidney by enhanced apoptosis and increased inflammatory reaction*" *Am. J. Pathol.* 160, 1181-1191]. An irregular organization of collagen fibrils in different human pathologies leading to phenotypes with fragile skin can also be observed, suggesting that the alteration of fibrillogenesis processes is enough to cause a fragile skin and a disorganized structure of the matrix, and consequently the individuals having a deregulated fibrillogenesis process have a higher incidence of injuries as well as of abnormal healing processes [Keene D. R., Ridgway C. C. and Iozzo R. V. (1998) "*Type VI microfilaments interact with a specific region of banded collagen fibrils in skin*" *J. Histochem. Cytochem.* 46, 215-220; Iozzo R. V. (1999) "*The biology of the small leucine-rich proteoglycans*" *J. Biol. Chem.* 274, 18843-18846].

Decorin not only interacts with collagen fibers, but also interacts with other structural proteins. This is presumably due to its horseshoe shaped three-dimensional structure, where the leucine-rich region repeats are arranged in parallel, only a few repeats being necessary for its binding to a ligand [Schonherr E., Broszat M., Brandan E., Bruckner P. and Kresse H. (1998) "*Decorin core protein fragment Leu155-Val260 interacts with TGF-beta but does not compete for decorin binding to type I collagen*" *Arch. Biochem. Biophys.* 355, 241-248]. From the results of molecular dynamics studies conducted it is inferred that the concave face of the decorin horseshoe has an opening with an angle sufficient to accommodate a triple helix, with a diameter of approximately 2 nm, which is slightly greater than the diameter of a collagen (1.5 nm), whereas the arms of the horseshoe have a thickness similar to the collagen molecule [Kresse H., Liszio C., Schonherr E. and Fisher L. W. (1997) "*Critical role of glutamate in a central leucine-rich repeat of decorin for interaction with type I collagen*" *J. Biol. Chem.* 272, 18404-18410; Scott J. E. (1996) "*Proteodermatan and proteokeratan sulfate (decorin, lumican/fibromodulin) proteins are horseshoe shaped. Implications for their interactions with collagen*" *Biochemistry* 35, 8795-8799].

The theoretical structural studies conducted consider the hypothesis that the $Lys^{130}$-$Arg^{133}$ and $Arg^{272}$-$His^{275}$ decorin regions are responsible for the binding to collagen, specifically the $Asp^{857}$-Arg-Gly-$Glu^{860}$ region [Kresse H., Liszio C., Schonherr E. and Fisher L. W. (1997) "*Critical role of glutamate in a central leucine-rich repeat of decorin for interaction with type I collagen*" *J. Biol. Chem.* 272, 18404-18410]. The two decorin regions are one in each arm of the horseshoe, approximately equidistant from the ends of the molecule, in an anti-parallel direction. However, the fact that decorin adopts a horseshoe shape makes the linear sequence rotate 180° of one arm of the horseshoe to the other arm, the two fragments actually being in a parallel arrangement. A complementarity of the charges of the side-chain residues involved in the interaction ([−,+,0,−] for collagen and [+,−,0,+] for the decorin fragments) is thus achieved, which seems to be critical for stabilizing the interaction between the two molecules [Scott J. E. (1996) "*Proteodermatan and proteokeratan sulfate (decorin, lumican/fibromodulin) proteins are horseshoe shaped. Implications for their interactions with collagen*" *Biochemistry* 35, 8795-8799].

Aging

The skin undergoes dramatic changes with age, including changes in its morphology, physiology and in its mechanical properties. The skin of babies is smooth and soft, with a thick layer of fat and a very thin protective layer of keratin, where the skin of the elderly is very thin and has many wrinkles, with a very small layer of fat. The extracellular matrix also experiences changes with age, and these contribute to the group of changes of the physical properties of the skin related to aging [Wiberg C., Klatt A. R., Wagener R., Paulsson M., Bateman J. F., Heinegard D. and Morgelin M. (2003) "*Complexes of matrilin-1 and biglycan or decorin connect collagen VI microfibrils to both collagen II and aggrecan*" *J. Biol. Chem.* 278, 37698-37704]. The prolonged exposure to the sun and the environmental contaminants accelerate the skin aging process since the exposure to UV rays inhibits the synthesis of collagen and fibronectin in fibroblasts and catalyzes collagen degradation by stimulating the synthesis of the enzymes degrading it (matrix metalloproteases). Changes in type I collagen molecules, which are the major components of the extracellular matrix of the dermis, have been described [Hunzelmann N., Ueberham U., Eckes B., Hermann K. and Krieg T. (1997) "*Transforming growth factor-beta reverses deficient expression of type (I) collagen in cultured fibroblasts of a patient with metageria*" *Biochim. Biophys. Acta.* 1360, 64-70].

The cosmetic industry has made important efforts to counteract this loss of functionality of the components of the extracellular matrix with age. The balance between the production and the degradation of essential biomolecules of the skin (collagen, for example) tends, with aging, towards degradation processes, and this leads to a progressive thinning and disorganization of the dermis causing flaccidity in the dermis with the subsequent formation of wrinkles. At a microscopic level, the collagen of aged skin (both chronologically aged skin—mature skin—and skin aged by prolonged exposure to the sun or to environmental contaminants) is characterized by having thick fibrils organized in a manner similar to bundles of cables, which are not as aligned as in young skin [Oikarinen A. (1990) "*The aging of the skin: chronoaging versus photoaging*" *Photodermatol. Photoimmunol. Photomed.* 7, 3-4]. Therefore, the methods allowing a better organization of collagen fibers will have a potential beneficial effect on mature skin or on aged skin, allowing it to partially recover the mechanical properties (elasticity, flexibility and firmness) lost with age or exposure to the sun and/or to environmental contaminants and having a better appearance, with less presence of wrinkles and smoother.

In addition to collagen, the dermal extracellular matrix also contains proteoglycans which are involved in the properties of tissues and are altered with aging. Among them, decorin is catabolized into a fragment which is known as decorunt, corresponding to a version of decorin which lacks the carboxy-terminal fragment. The skin with a fetal origin do not, however, have detectable decorunt levels, whereas the maximum decorunt levels are determined from 30 years onwards, which is the age from which aging signs start to be manifested. The capacity of decorunt to bind to a collagen molecule is 100 times less than of decorin alone, a factor which is correlated to the fact that decorunt precisely lacks one of the decorin regions which is essential for the binding to collagen [Wiberg C., Klatt A. R., Wagener R., Paulsson M., Bateman J. F., Heinegard D. and Morgelin M. (2003) "*Complexes of matrilin-1 and biglycan or decorin connect collagen VI microfibrils to both collagen II and aggrecan*" *J. Biol. Chem.* 278, 37698-37704]. Knowing that decorin affects collagen fibrillogenesis processes and regulates the diameter of fibrils, the appearance of decorunt can have an important effect on the elasticity and morphological differences between the collagen fibers of young skin and those of aged skin [Carrino D. A., Sorrell J. M. and Caplan A. I. (2000) "*Age-related changes in the proteoglycans of human skin*" *Arch. Biochem. Biophys.* 373, 91-101]. It has also been demonstrated that the synthesis of decorin is reduced in skin aged by prolonged exposure to the sun or to environmental contaminants [Bernstein E. F., Fisher L. W., Li K., LeBaron R. G., Tan E. M. and Uitto J. (1995) "*Differential expression of the versican and decorin genes in photoaged and sun-protected skin. Comparison by immunohistochemical and northern analyses*" *Lab. Invest.* 72, 662-669], therefore this type of skin has a disorganization of collagen. Therefore, the decrease of the functional decorin content of aged skin, either due to age or due to prolonged exposure to the sun and to environmental contaminants, is directly related to the formation of a destructured fibrillar collagen network leading to a skin which is fragile, less elastic and with less tensile strength.

Healing

Wound healing in adults is a complicated reparative process. The healing process starts with the recruitment of a variety of specialized cells for their transfer to the wound site, and involves extracellular matrix and basement membrane deposition, angiogenesis, selective protease activity and re-epithelization. An important component of the healing process in adult mammals is fibroblast stimulation to generate the extracellular matrix. This extracellular matrix is a main component of the connective tissue which is developed to repair the wound area.

The connective tissue which is formed during the healing process often has a fibrous nature. A scar is an abnormal morphological structure resulting from a previous injury or wound (such as, for example, an incision, an excision or a trauma) and is formed by a connective tissue which is predominantly a type I and II collagen matrix and fibronectin. In the skin, the scar consists of collagen fibers in an abnormal organization as well as of an excess collagen deposition. In mammals, when the scar is raised above the skin, having a bulging appearance, it is due to the fact that they contain excess collagen arranged in an irregular manner, and are classified as hypertrophic scars. A keloid is another form of pathological scarring which is not only raised above the surface of the skin, but also extends to beyond the limits of the original injury, and it also has an excessive amount of connective tissue which is organized in an abnormal manner, predominantly forming vortical bands of connective tissue. An analysis of the decorin content in hypertrophic scars shows that its concentration is only 25% of that found in healthy tissues [Scott P. G., Dodd C. M., Ghahary A., Shen J. and Tredget E. E. (1998) "*Fibroblasts from post-burn hypertrophic scar tissue synthesize less decorin than normal dermal fibroblasts*" *Clin. Sci.* (*Lond*). 94, 541-547], a fact which explains the irregular organization of the collagen present in hypertrophic scars.

Likewise, truncated forms of decorin have been detected in hypertrophic scars [Honda T., Matsunaga E., Katagiri K., and Shinkai H. (1986) "*The proteoglycans in hypertrophic scar*" *J. Dermatol.* 13, 326-333; Garg H. G., Lippay E. W, Burd D. A. R and Neame P. J. (1990) "*Purification and characterization of iduronic acid-rich and glucuronic acid-rich proteoglycans implicated in human post-burn keloid scar*" *Carbohydr. Res.* 207, 295-305], and it has been demonstrated that these truncated forms are not capable of regulating the formation of collagen fibrils in a fibrillogenesis assay [Carrino D. A., Önnerfjord P., Sandy J. D., CS-Szabo G., Scott P. G., Sorrell J. M., Heinegard D. and Caplan A. I. (2003) "*Age related changes in the proteoglycans of human skin*" *J. Biol. Chem.* 278, 17566-17572].

The presence of scars in the skin is a factor which is not aesthetically accepted by most human beings. The medical sector has made important efforts to develop minimally invasive surgical process, such as arthroscopies or laparoscopies, which not only decrease the risks of post-surgical complications but also have the advantage of leaving scars of very small sizes or hardly visible scars. Despite these efforts, most surgical interventions are still carried out by open surgery, such that the control of the correct healing process is still an extremely important issue. Preventing the formation of hypertrophic scars and/or keloids, which have an irregularly organized collagen, is one of the objectives of the cosmetic and dermopharmaceutical sector. Therefore, the methods allowing a better organization of collagen fibers will have a potential beneficial effect on scars, allowing them to soften their appearance.

Therefore, the cosmetic or dermopharmaceutical compositions containing molecules imitating the activity of decorin by interacting with collagen fibrils or fibers, regulating the fibrillogenesis process, are potential candidates for their use as anti-aging products for the purpose of increasing the elasticity, firmness, structuring and flexibility of the skin, or as coadjuvants in post-surgical treatments for the purpose of softening the appearance of scars.

There are different patents with a cosmetic or dermopharmaceutical application which mention decorin for the treatment or prevention of aging, as well as for softening the appearance of scars. Patent application US2003/0124152 describes the use of decorin in cosmetic or dermatological compositions for the treatment of intrinsic (due to the passage of time and to genetic factors) or extrinsic (due to prolonged exposure to the sun or to environmental factors such as ultraviolet (UV) radiation, chemical contaminants, cigarette smoke and pollution) aging. U.S. Pat. No. 5,510,328 describes the use of decorin in pharmaceutical compositions for reducing or inhibiting wound contraction, and U.S. Pat. No. 6,509,314 describes the use of decorin for preventing or reducing wound scarring. There are other patents describing plant extracts or compounds which stimulate the synthesis of endogenous decorin, such as, for example, those described in patents JP2004051508, FR2834462, EP1367988, U.S. Pat. No. 6,551,602, U.S. Pat. No. 6,455,057, U.S. Pat. No. 6,440, 434, U.S. Pat. No. 6,423,325, U.S. Pat. No. 6,287,553 and U.S. Pat. No. 6,042,841. Research works focused on the search for the domains of decorin binding to collagen have been published in the literature which describe some synthetic peptides which are capable of binding to collagen, and which could potentially have the same activity as decorin, but all the sequences correspond to native decorin fragments [Vides V. M., Laschinger C. A., Arora P. D., Lee W, Hakkinen L., Larjava H., Sodek J. and McCulloch C. A. (2005) "*Collagen phagocytosis by fibroblasts is regulated by decorin*" *J. Biol. Chem.* 280, 23103-23113; Schonherr E., Broszat M., Brandan E., Bruckner P. and Kresse H. (1998) "*Decorin core protein fragment Leu155-Val260 interacts with TGF-beta but does not compete for decorin binding to type I collagen*" *Arch. Biochem. Biophys.* 355, 241-248]. However, there is currently no reference to the use of peptides not contained in the native decorin sequence which imitate the action of decorin in its binding to collagen, regulating fibrillogenesis and aiding in maintaining a structured collagen network.

The applicant of the present invention has determined that the synthetic peptides of the invention are effective in regulating fibrillogenesis, thus imitating the function of decorin. The sequence of the peptides of the invention is not contained in the native decorin sequence, therefore they can be considered as peptide mimetics of the activity of decorin. It has been postulated in the literature that for their binding to collagen, and consequently the regulation of fibrillogenesis, the peptide sequences must have four amino acids with a [+,−,0,+] charge pattern [Scott J. E. (1996) "*Proteodermatan and proteokeratan sulfate (decorin, lumican/fibromodulin) proteins are horseshoe shaped. Implications for their interactions with collagen*" *Biochemistry* 35, 8795-8799], such that there is a charge complementarity with the $Asp^{857}$-Arg-Gly-$Glu^{860}$ collagen fragment which allows stabilizing the interaction. The applicant of the present invention has determined that not all the sequences complying said charge complementarity postulated by Scott are capable of regulating fibrillogenesis. While the synthetic peptide RELH, corresponding to the decorin sequence 272-275 complies with the charge pattern and is capable of regulating fibrillogenesis, peptides His-Asp-Ala-Arg, Orn-Asp-Nva-His, His-Asp-Ile-His also comply with the charge pattern but have no effect on fibrillogenesis. Therefore, the compliance with the [+,−,0,+] charge pattern postulated by Scott is not a sufficient requirement for the regulation of fibrillogenesis by the peptides complying with it. The studies conducted by the applicant of the present invention have surprisingly established that the regulation of fibrillogenesis is determined by the peptide sequences having a citrulline amino acid residue together with a [+,−,0] charge pattern, such as, for example, the sequences Lys-Asp-Ile-Cit or Lys-Asp-Val-Cit. Patent RU2,181,728 describes a synthetic peptide of 10 amino acids bound by means of a disulfide bond to a peptide of 12 amino acids having a sequence including the sequence Lys-Glu-Leu-Cit, which is based on the interleukin-8 molecule and stimulates the migration of neutrophils. Despite the fact that said peptide complies with the [+,−,0] charge pattern and has a contiguous citrulline residue, it is not included within the family of the peptides of the present invention since it has a total of 22 amino acids. Furthermore, said patent does not give any indication nor suggest that the peptide described is capable of inhibiting fibrillogenesis.

Therefore, there is no indication in the state of the art that citrulline is a necessary residue for the regulation of fibrillogenesis, therefore a person skilled in the art could not deduce the nature of the peptides regulating fibrillogenesis.

Therefore, the peptides of the present invention can be useful in the treatment of the skin conditions requiring a regulation of fibrillogenesis, such as the treatment of aged skin (either due to age or due to exposure to the sun and/or to environmental contaminants) or as coadjuvants in healing processes to soften the appearance of scars.

DESCRIPTION OF THE INVENTION

The present invention provides a simple, effective and risk-free solution for the treatment of skin conditions requiring a regulation of fibrillogenesis, such as aging or scarring, comprising the application on skin of a cosmetic or dermopharmaceutical composition containing at least one peptide of general formula (I). In the context of the present invention, the term "treatment" relates to the reduction, delay and/or prevention of aging signs or to the softening of the appearance of scars. The term "aging" relates to changes experiences by the skin with age (chronoaging) or due to exposure to the sun (photoaging) or to environmental agents such as cigarette smoke, extreme climatic conditions of cold or wind, chemical contaminants or pollution, and includes all the external visible changes as well as those which can be perceived by touch, such as for example and in a non-limiting sense, the development of discontinuities in the skin such as wrinkles, fine lines, cracks, irregularities or roughness, increase in pore size, loss of elasticity, loss of firmness, loss of smoothness, loss of the capacity to recover from deformation, sagging of the skin such as sagging of the cheeks, the appearance of bags under the eyes or the appearance of double chin, among others, changes in the color of the skin such as spots, redness, dark circles or the appearance of hyperpigmented areas such as age spots or freckles, among others, anomalous differentation, hyperkeratinization, elastosis, keratosis, hair loss, loss of the structuring of collagen and other histological changes of the stratum corneum, of the dermis, of the epidermis, of the vascular system (for example, the appearance of spider veins or telangiectasias) or of the tissues close to the skin, among others.

Therefore, a primer aspect of this invention relates to a peptide capable of regulating fibrillogenesis, according to the general formula (I):

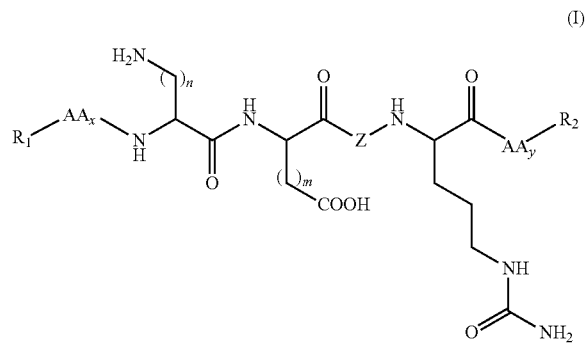

(I)

stereoisomers thereof and mixtures thereof, which may or may not be racemic, and the cosmetically or dermopharmaceutically acceptable salts thereof, wherein:

Z is selected from the group consisting of alanyl, allo-isoleucyl, glycyl, isoleucyl, isoseryl, isovalyl, leucyl, norleucyl, norvalyl, prolyl, seryl, threonyl, allo-threonyl or valyl;

n and m may vary independently from one another between 1 and 5;

AA is selected from the group consisting of natural amino acids encoded in their L- or D-form or non-encoded amino acids;

x and y may vary independently from one another between 0 and 2;

$R_1$ is selected from the group consisting of H or alkyl, aryl, aralkyl or acyl group; and $R_2$ is selected from the group consisting of amino, hydroxyl or thiol, substituted or non-substituted with aliphatic or cyclic groups.

The preferred structures of the peptides shown in the general formula (I) are those wherein:

Z may be: isoleucyl, threonyl or valyl;

$R_1$ may be: H or linear, branched or cyclic, saturated or unsaturated $C_2$ to $C_{24}$ acyl; and $R_2$ may be: amino or hydroxyl, substituted or non-substituted with linear, branched or cyclic, saturated or unsaturated $C_1$ to $C_{24}$ aliphatic groups.

The peptides of the present invention can exist as stereoisomers or mixtures of stereoisomers; for example, the amino acids forming them can have an L-, D-configuration, or can be racemic independently from one another. It is therefore possible to obtain isomeric mixtures as well as racemates or diastereoisomeric mixtures, or pure diastereoisomers or enantiomers, depending on the number of asymmetric carbons and on which isomers or isomeric mixtures are present.

The preferred structures of the peptides of general formula (I) are pure isomers, i.e., enantiomers or diastereoisomers.

In the context of the present invention, the term "non-encoded amino acids" relates to the amino acids which are not encoded by the genetic code, either natural or non-natural, such as for example and in a non-limiting sense, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statin, norleucine, N-methylamino acids, β-amino acids or γ-amino acids among others, as well as their derivatives. A list of non-natural amino acids can be found in the article "Unusual amino acids in peptide synthesis" by D. C. Roberts and F. Vellaccio, in The Peptides, Vol. 5 (1983), Chapter VI, Gross E. and Meienhofer J., Eds., Academic Press, New York, USA, or in commercial catalogs of the specialized companies in the sector, such as for example NeoMPS, Bachem, Novabiochem, Sigma-Aldrich, Peptides International, Advanced ChemTech, Chem-Impex, Maybridge Chemical, Chirotech Technology, Peninsula Laboratories or RSP Amino Acid Analogues, among others.

In the context of the present invention, when x and y are different from 0, it is clearly understood that the nature of AA does not make the activity of the peptides of the invention difficult, but rather it contributes in the regulation of fibrillogenesis or has no effect on it.

In the context of the present invention, the term "aliphatic group" relates to a saturated or unsaturated, linear or cyclic hydrocarbon group.

The term "hydrocarbon group" is used in the present invention to cover alkyl, alkenyl or alkynyl groups for example.

The term "alkyl group" relates to a saturated, linear or branched hydrocarbon group, including, for example, methyl, ethyl, isopropyl, isobutyl, t-butyl, heptyl, dodecyl, hexadecyl, octadecyl, amyl, 2-ethylhexyl, 2-methylbutyl, 5-methylhexyl and the like.

The term "alkenyl group" relates to an unsaturated, linear or branched hydrocarbon group with one or more carbon-carbon double bonds, such as the vinyl group.

The term "alkynyl group" relates to an unsaturated, linear or branched hydrocarbon group with one or more carbon-carbon triple bonds.

The term "cyclic group" relates to a closed hydrocarbon ring, which can be classified as an alicyclic, aromatic or heterocyclic group.

The term "alicyclic group" relates to a cyclic hydrocarbon group with properties similar to aliphatic groups.

The term "aromatic group" or "aryl group" relates to a mono- or polycyclic aromatic hydrocarbon group.

The term "heterocyclic group" relates to a closed hydrocarbon ring, in which one or more than one of the atoms of the ring is an element different from carbon (for example, nitrogen, oxygen, sulfur, etc.).

As understood in this technical area, the existence of a high degree of substitution is not only tolerated but recommended. Therefore, there may be substitution in the peptides of the present invention. For the purpose of simplifying the present description of the invention, the terms "group" and "block" will be used to distinguish between chemical species allowing substitution or which can be substituted ("group"), and those which do not allow substitution or which cannot be substituted ("block"). In this way, when the term "group" is used to describe a chemical substituent, the described chemical material includes both the non-substituted group and that containing the O, N or S atoms.

In addition, when the term "block" is used to describe a chemical compound or substituent, only non-substituted chemical material can be included. For example, the expression "alkyl group" will not only include open-chain saturated alkyl compounds, such as methyl, ethyl, propyl, isobutyl and the like, but also alkyl substituents containing other substituents known in the state of the art, such as hydroxy, alkoxy, amino, carboxyl, carboxamido, halogen atoms, cyano, nitro, alkylsulfonyl, and others. "Alkyl group" thus includes ether, haloalkyl, alcohol, thiol, carboxyl, amine, hydroxyalkyl, sulfoalkyl, guanidine groups and others. In addition, the expression "alkyl block" is only limited to the inclusion of open-chain saturated alkyl substituents, such as methyl, ethyl, propyl, isobutyl and the like.

The cosmetically or dermopharmaceutically acceptable salts of the peptides of formula (I) provided by this invention are within the scope of the present invention. The term "cosmetically or dermopharmaceutically acceptable salts" includes the salts usually used to form metal salts or acid addition salts, either organic (such as for example and in a non-limiting sense, acetate, citrate, oleate, oxalate or gluconate) or inorganic (such as for example and in a non-limiting sense, chloride, sulfate, borate or carbonate). The nature of the salt is not critical, provided that it is cosmetically or pharmaceutically acceptable. The cosmetically or pharmaceutically acceptable salts of the peptides of formula (I) can be obtained by conventional methods that are well known in the state of the art.

The synthesis of the peptides of general formula (I) can be carried out according to conventional methods known in the state of the art, such as for example, the adaptation of solid-phase peptide synthesis methods [Stewart J. M. and Young J. D. (1984) "*Solid Phase Peptide Synthesis, 2nd edition*", Pierce Chemical Company, Rockford, Ill. Bodanzsky M. and Bodanzsky A. (1984) "*The practice of Peptide Synthesis*", Springer Verlag, New York; Lloyd-Williams, P., Albericio, F. and Giralt, E. (1997) "*Chemical Approaches to the Synthesis of Peptides and Proteins*" CRC, Boca Raton (Fla., USA)], solution synthesis, a combination of solid-phase synthesis and solution synthesis methods or enzymic synthesis methods [Kullmann W. (1980) "*Proteases as catalysts for enzymic*

*syntheses of opioid peptides" J. Biol. Chem.* 255, 8234-8238]. The peptides can also be obtained by the fermentation of a bacterial strain that is modified or unmodified by genetic engineering with the aim of producing the desired sequences.

For example, a method for obtaining the peptides of general formula (I) is that in which a fragment of the peptide of general formula (I) having a free carboxyl group or a reactive derivative thereof is reacted with a complementary fragment having an amino group with at least one free hydrogen atom, with the subsequent formation of an amide type bond, and wherein the functional groups of said fragments that do not participate in the formation of the amide type bond, if they exist, are conveniently protected with temporary or permanent protective groups.

Another example of a method for obtaining the peptides of general formula (I) is that in which a fragment of the peptide of general formula (I) having a leaving group, such as for example the tosyl group, the mesyl group and halogen groups, among others, is reacted with a complementary fragment having an amino group with at least one free hydrogen atom by means of a nucleophilic substitution reaction, and wherein the functional groups of said fragments that do not participate in the formation of the N—C bond, if they exist, are conveniently protected with temporary or permanent protective groups. Examples of protective groups, their insertion and elimination are described in the literature [Greene T. W. (1981) *"Protective groups in organic synthesis"* John Wiley & Sons, New Cork; Atherton B. and Sheppard R. C. (1989) *"Solid Phase Peptide Synthesis: A practical approach"* IRL Oxford University Press]. The term "protective groups" also includes the polymeric supports used in solid-phase synthesis.

When the synthesis is carried out completely or partially in solid phase, the following can be mentioned as solid supports to be used in the method of the invention: supports made of polystyrene, polyethylene glycol-grafted polystyrene and the like, such as for example p-methylbenzhydrylamine resins (MBHA) [Matsueda G. R. and Stewart J. M. (1981) *"A p-methylbenzhydrylamine resin for improved solid-phase synthesis of peptide amides" Peptides* 2, 45-50], 2-chlorotrityl resins [Barlos K., Gatos D., Kallitsis J., Papaphotiu G., Sotiriu P., Wenqing Y. and Schäfer W. (1989) *"Darstellung geschützter peptid-fragmente unter einsatz substituierter triphenylmethyl-harze" Tetrahedron Lett.* 30, 3943-3946; Barlos K., Gatos D., Kapolos S., Papaphotiu G., Schäfer W. and Wenqing Y. (1989) *"Veresterung von partiell geschützten peptidfragmenten mit harzen. Einsatz von 2-chlorotritylchlorid zur synthese von Leu15-gastrin I" Tetrahedron Lett.* 30, 3947-3951], TentaGel® resins and the like, which may or may not include a labile spacer such as 5-(4-aminomethyl-3,5-dimethoxyphenoxy) valeric acid (PAL) [Albericio F., Kneib-Cordonier N., Biancalana S., Gera L., Masada R. I., Hudson D. and Barany G. (1990) *"Preparation and application of the 5-(4-(9-fluorenylmethyloxycarbonyl)aminomethyl-3,5-dimethoxy-phenoxy)-valeric acid (PAL) handle for the solid-phase synthesis of C-terminal peptide amides under mild conditions" J. Org. Chem.* 55, 3730-3743], 2-[4-*aminomethyl*-(2,4-*dimethoxyphenyl*)*phenoxyacetic acid* (*AM*) [Rink H. (1987) *"Solid-phase synthesis of protected peptide fragments using a trialkoxy-diphenyl-methylester resin" Tetrahedron Lett.* 28, 3787-3790], Wang [Wang S. S. (1973) *"p-Alkoxybenzyl Alcohol Resin and p-Alkoxybenzyloxycarbonylhydrazide Resin for Solid Phase Synthesis of Protected Peptide Fragments" J. Am. Chem. Soc.* 95, 1328-1333] and the like, allowing the deprotection and simultaneous cleavage of the compound from the polymeric support.

The peptides according to the invention can form part of various types of compositions for their external application in the body of a mammal, preferably human beings. In this sense, the invention provides a cosmetic or dermopharmaceutical composition comprising at least one peptide of general formula (I). Said compositions can be prepared by means of conventional methods known by persons skilled in the art.

The peptides object of the present invention have a variable water-solubility, according to the nature of the $R_1$, $R_2$, AA and Z groups and the values of n, m, x and y. Those which are not water-soluble can be solubilized in conventional cosmetically or dermopharmaceutically acceptable solvents such as for example ethanol, propanol or isopropanol, propylene glycol, glycerin, butylene glycol or polyethylene glycol or any combination thereof. The peptides can also be previously incorporated into cosmetic or pharmaceutical delivery systems and/or sustained release systems such as for example and in a non-limiting sense, liposomes, milliparticles, microparticles and nanoparticles as well as sponges, vesicles, micellae, millispheres, microspheres and nanospheres, liposheres, millicapsules, microcapsules and nanocapsules, for the purpose of achieving a greater penetration of the active ingredient. Likewise, the peptides of the present invention can also be adsorbed on solid organic polymers or mineral supports such as talc, bentonite, silica, starch or maltodextrin, among others.

These preparations can be used in different types of formulations such as for example creams, emulsions of oil and silicone in water, emulsions of oil in water, emulsions of silicone in water, emulsions of water in oil and silicone, emulsions of water in oil, emulsions of water in silicone, oils, milks, balms, foams, lotions, gels, liniments, serums, soaps, unguents, mousses, ointments, bars, pencils or sprays, including leave on and rinse-off formulations, and can also be incorporated by means of techniques known by persons skilled in the art to different types of solid accessories such as wet wipes, hydrogels, adhesive (or non-adhesive) patches or face masks, or can be incorporated into different make-up line products such as concealers, make-up foundations, make-up removal milks or lotions, eye shadows and lipsticks among others.

The peptides can also be incorporated into fabrics for making garments which are in direct contact with the skin of the body, such that the peptides of the invention are released either by the biodegradation of the system of anchoring to the fabric or by the friction of the garment with the body, by body moisture, by the pH of the skin or by body temperature. Examples of garments, fabrics and means for immobilizing the peptides in the fabric, including microencapsulation, are described in the literature and are known in the state of the art [Schaab C. K. (1986) *"Impregnating Fabrics With Microcapsules", HAPPI* May 1986; Nelson G. (2002) *"Application of microencapsulation in textiles" Int. J. Pharm.* 242, 55-62]. Preferred garments are bandages, girdles, pantyhose, socks, panties, brassieres and bands for arms and forearms.

The cosmetic or pharmaceutical composition object of the present invention can be applied in the areas of the body requiring treatment by means of subcutaneous injection, intradermal injection, steam wrap or by means of iontophoresis for the purpose of achieving a greater penetration of the active ingredient. The preferred areas for the application are face, neck, forearms, chest, buttocks, abdomen and thighs.

The compositions mentioned in the present invention can contain additional ingredients commonly used in compositions for the care and treatment of the skin, such as for example and in a non-limiting sense, emulsion agents, emollients, organic solvents, skin conditioners such as for example, humectants, alpha-hydroxy acids, moisturizers, vitamins, pigments or dyes, gelling polymers, thickeners, softeners, anti-wrinkle agents, agents capable of reducing or treating bags under the eyes, whitening or depigmenting agents, exfoliating agents, anti-aging agents, anti-free radical agents and/or anti-atmospheric pollution agents, NO-synthase inhibiting agents, antioxidant agents, anti-glycation agents, agents stimulating the synthesis of dermal or epidermal macromolecules and/or capable of inhibiting their degradation, such as for example agents stimulating the synthesis of collagen, agents stimulating the synthesis of elastin, agents stimulating the synthesis of laminin, agents stimulating the synthesis of decorin, agents inhibiting collagen degradation, agents inhibiting elastin degradation, agents stimulating fibroblast proliferation, agents stimulating keratinocyte proliferation, agents stimulating keratinocyte differentiation, agents stimulating the synthesis of lipids and components of the stratum corneum (ceramides, fatty acids etc.), dermorelaxant agents, agents stimulating the synthesis of glycosaminoglycan, refirming agents, anti-stretch mark agents, calming agents, anti-inflammatory agents, agents acting on capillary circulation and/or microcirculation, agents acting on cell metabolism, agents stimulating and/or inhibiting the synthesis of melanin, agents that improve the dermal-epidermal junction, anti-microbial agents, preservatives, perfumes, chelating agents, plant extracts, essential oils, marine extracts, agents produced by biofermentation, mineral salts, cell extracts and sunscreens (organic or mineral photoprotective agents that are active against ultraviolet A and B rays), among others, provided that they are physically and chemically compatible with the rest of the components of the composition and especially with the peptides of general formula (I) of the present invention. The nature of said additional ingredients can be synthetic or natural, such as for example plant extracts.

Likewise, the compositions of the present invention can contain or can be co-administered with analgesic compounds and/or anti-inflammatory compounds for the purpose of reducing the swelling and the irritation associated to both sensitive skin and to healing processes or for treating hypertrophic or keloid scars. Steroidal type compounds such as hydrocortisone, non-steroidal type compounds such as paracetamol or acetylsalicylic acid or natural extracts or essential oils with intrinsic analgesic and anti-inflammatory activity can be emphasized among said compounds.

An additional aspect of the present invention relates to a cosmetic or dermopharmaceutical composition comprising a cosmetically or dermopharmaceutically effective amount of at least one peptide according to the general formula (I), and furthermore a cosmetically or dermopharmaceutically effective amount of at least one extract with anti-wrinkle and/or anti-aging activity such as for example and in a non-limiting sense, *Vitis vinifera, Rosa canina, Curcuma longa, Iris pallida, Theobroma cacao, Ginkgo biloba*, or *Dunaliella salina* extracts, among others or of furthermore at least one synthetic compound, extract or biofermentation product with anti-wrinkle and/or anti-aging activity as for example and in a non-limiting sense Matrixyl® marketed by Sederma, Vialox® or Syn-ake® marketed by Pentapharm, Myoxinol™ marketed by Cognis, Algisum C® or Hydroxyprolisilane CN®, marketed by Exsymol, Argireline®, Leuphasyl®, Aldenine® or Lipochroman® marketed by Lipotec, Kollaren® marketed by Institut Europeen de Biologie Cellulaire, Collaxyl® or Quintescine® marketed by Vincience, $Ca^{2+}$ channel antagonists such as alverine, manganese or magnesium salts, certain secondary or tertiary amines, retinol and its derivatives, idebenone and its derivatives, Coenzyme Q10 and its derivatives, boswellic acid and its derivatives, gamma-aminobutyric acid or chloride channel agonists among others.

An additional aspect of the present invention relates to a cosmetic or dermopharmaceutical composition comprising a cosmetically or dermopharmaceutically effective amount of at least one peptide according to the general formula (I), and furthermore a cosmetically or dermopharmaceutically effective amount of at least one extract or combination of extracts with refirming, redensifying and/or restructuring activity such as for example and in a non-limiting sense, *Malpighia punicitolia, Cynara scolymus, Gossypium herbaceum, Aloe Barbadensis, Panicum miliaceum, Morus nigra, Sesamum indicum, Glycine soja, Triticum vulgare* extracts, Pronalen®Refirming HSC or Polyplan®Refirming marketed by Provital, Lanablue® marketed by Atrium, Pepha®-Nutrix marketed by Pentapharm, or plant extracts containing isoflavones such as Phyto-Flavone® marketed by Vichy, among others, or of furthermore at least one synthetic compound, extract or biofermentation product with refirming, redensifying and/or restructuring activity such as for example and in a non-limiting sense, Biopeptide EL™, Biopeptide CL™, Vexel®, Matrixyl® or Bio-Bustyl™ marketed by Sederma, Dermosaccharides®HC, Aglycal®, Cytokinol®LS or Firmiderm®LS9120 marketed by Laboratoires Serobiologiques, Liftline®, Raffermine® or Ridulisse C® marketed by Silab, Serilesine® marketed by Lipotec, Ursolisome®, Basaline® or Collalift® marketed by Coletica/Engelhard, Syn®-Coll marketed by Pentapharm, Hydriame® marketed by Atrium or IP2000® marketed by Institut Europeen de Biologie Cellulaire, among others.

An additional aspect of the present invention relates to a cosmetic or dermopharmaceutical composition comprising a cosmetically or dermopharmaceutically effective amount of at least one peptide according to the general formula (I), and furthermore a cosmetically or dermopharmaceutically effective amount of at least one extract or combination of extracts with healing or re-epithelizing activity or with efficacy as coadjuvants in healing or re-epithelization processes such as for example and in a non-limiting sense, *Centella asiatica, Rosa moschata, Echinacea angustifolia, Symphytum officinal, Equisetum arvense, Hypericum perforatum, Mimosa tenuiflora*, Aloe vera extracts, Polyplant® Epithelizing marketed by Provital, Cytokinol® LS 9028 marketed by Pentapharm or Deliner® marketed by Coletica/Engelhard, among others, or of furthermore at least one synthetic compound, extract or biofermentation product with healing or re-epithelizing activity or with efficacy as a coadjuvant in healing or re-epithelizing processes such as for example and in a non-limiting sense, Antarcticine® marketed by Lipotec, among others.

The peptides of general formula (I) are used in the cosmetic or dermopharmaceutical compositions of the present invention at cosmetically or pharmaceutically effective concentrations to achieve the desired effect; preferably between 0.000001% (by weight) and 20% (by weight); more preferably between 0.00001% (by weight) and 10% (by weight) and even more preferably between 0.0001% (by weight) and 5% (by weight).

Therefore, an additional aspect of this invention relates to the use of at least one peptide of general formula (I) in the preparation of a cosmetic or dermopharmaceutical composition for its application on the skin, preferably for the treatment of those skin conditions requiring a regulation of fibrillogenesis such as the treatment of aged skin (either due to age or due to exposure to the sun and/or to environmental contaminants) or as coadjuvants in healing processes to soften the appearance of scars. The preferred applications are the application in thighs, abdomen, buttocks, chest, forearms, neck and face, or on those areas of the body that have scars.

The present invention further provides a cosmetic or dermopharmaceutical method for treating those skin conditions requiring a regulation of fibrillogenesis, preferably the skin of humans, comprising the administration of an effective amount of peptides of general formula (I), preferably in the form of a cosmetic or dermopharmaceutical composition containing them. The frequency of application on the skin can vary extensively, depending on the needs of each subject, a range of application from once a month up to 10 times a day, preferably from once a week up to 4 times a day, preferably from three times a week up to twice a day, even more preferably once a day, is suggested.

A preferred cosmetic or dermopharmaceutical method is that in which the object of the regulation of fibrillogenesis is to reduce, delay and/or prevent the aging signs or soften the appearance of scars.

EXAMPLES

The following specific examples provided herein are useful for illustrating the nature of the present invention. These examples are included solely for illustrative purposes and must not be interpreted as limitations to the invention claimed herein.

General Methodology

Chemical Synthesis

All the synthetic processes are carried out in polypropylene syringes equipped with porous polyethylene disks. All the reagents and solvents are of a quality for synthesis and are used without any additional treatment. The solvents and reagents are eliminated by suction. The elimination of the Fmoc group is carried out with piperidine-DMF (2:8, v/v) (1×1 min, 1×5 min; 5 mL/g resin) [Lloyd-Williams P., Albericio F. and Giralt, E. (1997) "*Chemical Approaches to the Synthesis of Peptides and Proteins*" CRC, Boca Raton (Fla., USA)]. The washings between the steps of deprotection, coupling and once again deprotection have been carried out with DMF (3×1 min) using 10 mL of solvent/g of resin each time. The coupling reactions have been carried out with 3 mL of solvent/g of resin. The control of the couplings is carried out by means of the ninhydrin test [Kaiser E., Colescott R. L., Bossinger C. D. and Cook P. I. (1970) "*Color test for detection of free terminal amino groups in the solid-phase synthesis of peptides*" Anal. Biochem. 34, 595-598]. All the synthetic transformations and washings have been carried out at 25° C.

The chromatographic analysis by HPLC was carried out in Shimadzu equipment (Kyoto, Japan) using a reversed-phase column thermostatted at 30° C. (250×4.0 mm, Kromasil $C_8$, 5 µm, Akzo Nobel, Sweden). The elution was carried by means of a gradient of acetonitrile (+0.07% TFA) in water (+0.1% TFA) at a flow of 1 mL/min and the detection was carried out at 220 nm.

Abbreviations:

The abbreviations used for the amino acids follow the rules of the IUPAC-IUB Commission on Biochemical Nomenclature specified in *Eur. J. Biochem.* (1984) 138, 9-37 and in *J. Biol. Chem.* (1989) 264, 633-673.

Ac, acetyl; AM, 2-[4-aminomethyl-(2,4-dimethoxyphenyl)-phenoxyacetic acid; Boc, tert-butyloxycarbonyl; Cit, citrulline; Dap, 2,3-diaminopropionic acid; DCM, dichloromethane; DIEA, N,N-diisopropylethylamine; DIPCDI, N,N'-diisopropylcarbodiimide; DMF, N,N-dimethylformamide; equiv, equivalents; DPPC, dipalmitoylphosphatidylcholine; ES-MS, electrospray mass spectrometry; Fmoc, fluorenylmethoxycarbonyl; GAGs, glycosaminoglycans; HOBt, 1-hydroxybenzotriazole; HPLC, high performance liquid chromatography; MBHA, p-methylbenzhydrylamine resin; MeCN, acetonitrile; MeOH, methanol; MLV, multilaminar vesicles; Nva, norvaline; Orn, ornithine; Palm, palmitoyl; tBu, tert-butyl; TFA, trifluoroacetic acid; TGF-β, transforming growth factor-β; THF, tetrahydrofuran; TIS, triisopropylsilane; ULV, unilaminar vesicles.

Example 1 (Prophetic)

Obtaining Palm-Dap-Glu-Ile-Cit-OH 3.5 g of Fmoc-L-Cit-OH (8.8 mmol, 1 equiv) dissolved in 55 mL of DCM to which 1.3 mL of DIEA (7.6 mmol, 0.86 equiv) have been added, are incorporated to the dry 2-chlorotrityl resin (5.5 g, 8.8 mmol). It is left stirring for 5 minutes, after which 2.5 mL of DIEA (14.6 mmol, 1.66 equiv) are added. It is allowed to react for 40 minutes. The remaining chloride groups are blocked by treatment with 4.4 mL of MeOH.

The amino terminal Fmoc group is deprotected as described in general methods and 7.77 g of Fmoc-L-Ile-OH (22 mmol, 2.5 equiv) are incorporated to the peptidyl-resin in the presence of DIPCDI (3.39 mL, 22 mmol, 2.5 equiv) and HOBt (3.37 g, 22 mmol, 2.5 equiv) using DMF as a solvent for 1 hour. The resin is subsequently washed as described in general methods and the treatment for deprotecting the Fmoc group is repeated to incorporate the next amino acid. By following the described protocols, 9.36 g of Fmoc-L-Glu (OtBu)-OH (22 mmol, 2.5 equiv) and 9.38 g of Fmoc-L-Dap (Boc)-OH (22 mmol, 2.5 equiv) are sequentially coupled in the presence in each coupling of 3.37 g of HOBt (22 mmol, 2.5 equiv) and 3.39 mL of DIPCDI (22 mmol, 2.5 equiv).

The N-terminal Fmoc group is deprotected as described in general methods, and 22.5 g of palmitic acid (88 mmol, 10 equiv) predissolved in DMF (10 mL) were incorporated in the presence of 13.55 g of HOBt (88 mmol, 10 equiv) and 13.55 mL of DIPCDI (88 mmol, 10 equiv). It is allowed to react for 15 hours, after which the resin is washed with THF (5×1 min), DCM (5×1 min), DMF (5×1 min), MeOH (5×1 min), DMF (5×1 min), THF (5×1 min), DMF (5×1 min), DCM (4×1 min), ether (3×1 min), and vacuum-dried.

12.36 g of the dry peptidyl-resin are treated with 87 mL of TFA-TIS-$H_2O$ (90:5:5) for 2 hours at room temperature. The filtrates are collected on cold diethyl ether (700 mL), filtered through a porous plate and the precipitate is washed with ether (500 mL) 5 times. The final precipitate is vacuum-dried.

Example 2

Synthesis of H-Lys-Asp-Val-Cit-$NH_2$ 0.685 mg of the Fmoc-AM-MBNA resin with a functionalization of 0.73 mmol/g (0.5 mmol) with piperidine-DMF according to the described general protocol for the purpose of eliminating the Fmoc group. 0.99 g of Fmoc-L-Cit-OH (2.5 mmol, 5 equiv) were incorporated to the deprotected resin in the presence of DIPCDI (385 µL, 2.5 mmol, 5 equiv) and HOBt (385 mg, 2.5 mmol, 5 equiv) using DMF as a solvent for 1 hour.

The resin was subsequently washed as described in general methods and the treatment for deprotecting the Fmoc group was repeated to incorporate the next amino acid. By following the described protocols, 0.85 g of Fmoc-L-Val-OH (2.5 mmol, 5 equiv), 1.03 g of Fmoc-L-Asp(OtBu)-OH (2.5 mmol, 5 equiv) and 1.17 g of Fmoc-L-Lys(Boc)-OH (2.5 mmol, 5 equiv) were sequentially coupled in the presence in each coupling of 385 mg of HOBt (2.5 mmol, 5 equiv) and 385 µL of DIPCDI (2.5 mmol, 5 equiv).

The N-terminal Fmoc group was deprotected as described in the general methods, washed with DMF (5×1 min), DCM (4×1 min), diethyl ether (4×1 min) and vacuum-dried.

1.17 g of the dry peptidyl-resin were treated with 15 mL of TFA-TIS-H$_2$O (90:5:5) for 2 hours at room temperature. The filtrates were collected on cold diethyl ether (100 mL), centrifuged for 5 minutes at 4000 rpm and the ether solution was decanted. The washings with ether were repeated 5 times. The final precipitate was vacuum-dried.

The analysis by HPLC in a gradient from 5 to 95% of MeCN (+0.07% TFA) in H$_2$O (+0.1% TFA) showed a purity greater than 70%. Its molecular weight was determined by ES-MS [(M+H)$^+_{theoretical}$ 517.59, (M+H)$^+_{exp}$ 517.7].

Example 3 (Prophetic)

Obtaining Ac-Orn-Asp-Thr-Cit-NH—(CH$_2$)$_9$—CH$_3$ 1.28 g of Fmoc-L-Cit-OH (3.23 mmol, 1 equiv) dissolved in 20 mL of DCM to which 500 µL of DIEA (2.9 mmol, 0.90 equiv) have been added, are incorporated to the dry 2-chlorotrityl resin (2.0 g, 3.3 mmol). It is left stirring for 5 minutes, after which 1 mL of DIEA (5.9 mmol, 1.81 equiv) is added. It is allowed to react for 40 minutes. The remaining chloride groups are blocked by treatment with 1.6 mL of MeOH.

On 1 mmol of the aminoacyl-resin, the amino terminal Fmoc group is deprotected as described in general methods and 1.99 g of Fmoc-L-Thr(tBu)-OH (5 mmol, 5 equiv) are incorporated in the presence of DIPCDI (770 µL, 5 mmol, 5 equiv) and HOBt (770 mg, 5 mmol, 5 equiv) using DMF as a solvent for 1 hour. The resin is subsequently washed as described in general methods and the treatment for deprotecting the Fmoc group is repeated to incorporate the next amino acid. By following the described protocols, 2.06 g of Fmoc-L-Asp(OtBu)-OH (5 mmol, 5 equiv) and 2.27 g of Fmoc-L-Orn(Boc)-OH (5 mmol, 5 equiv) are sequentially coupled in the presence in each coupling of 770 mg of HOBt (5 mmol, 5 equiv) and 770 µL of DIPCDI (5 mmol, 5 equiv).

The N-terminal Fmoc group is deprotected as described in general methods, the peptidyl-resin is treated for 30 minutes with 2.36 mL of acetic anhydride (25 mmol, 25 equiv) in the presence of 4.28 mL of DIEA (25 mmol, 25 equiv) using DMF as a solvent, washed with DMF (5×1 min), DCM (4×1 min), diethyl ether (4×1 min) and vacuum-dried.

The completely protected peptide, [Ac-L-Orn(Boc)-L-Asp(OtBu)-L-Thr(tBu)-L-Cit-OH], is obtained by the treatment for 5 minutes of the peptidyl-resin, previously dried under vacuum in the presence of KOH, with a 3% solution of TFA in DCM. The filtrates are collected on cold diethyl ether and the treatment is repeated three times. The ether solutions are rotary evaporated to dryness at room temperature, the precipitate is resuspended in 50% MeCN in H$_2$O and lyophilized. 279 mg of the crude product obtained (367 µmol) are weighed in a balloon, 350 mg of decylamine (3 equiv) and 30 mL of anhydrous DMF are added. 120 µL of DIPCDI (2 equiv) are added and it is allowed to react with magnetic stirring at 47° C. The reaction is controlled by means of HPLC by the disappearance of the initial product, being complete after 24 hours. The solvent is evaporated to dryness and co-evaporated twice with DCM. The residue obtained [Ac-L-Orn(Boc)-L-Asp(OtBu)-L-Thr(tBu)-L-Cit-NH—(CH$_2$)$_9$—CH$_3$] is resuspended in 50 mL of a mixture of TFA-DCM-anisole (49:49:2) and it is allowed to react for 30 minutes at room temperature. 250 mL of cold diethyl ether are added, the solvent is rotary evaporated and two additional co-evaporations are carried out with ether. The residue is dissolved in a 50% mixture of MeCN in H$_2$O and lyophilized.

The analysis by HPLC in a gradient from 5 to 95% of MeCN (+0.07% TFA) in H$_2$O (+0.1% TFA) indicates a purity greater than 70%. Its molecular weight is determined by ES-MS [(M+H)$^+_{theoretical}$ 686.8].

Example 4

Starting from an EFT-200 three-dimensional human skin model (MatTek Corporation), the tissues were treated with H-Lys-Asp-Ile-Cit-NH$_2$ and with H-Lys-Asp-Val-Cit-NH$_2$ at a concentration of 0.1 mg/mL in culture medium. The latter was changed daily for 14 days, adding peptide at the same concentration in each change. On day 14, the tissues were fixed with a solution of 2% paraformaldehyde and 2.5% glutaraldehyde in 0.1M phosphate buffer, pH 7.4, for at least 2 hours at 4° C. The post-fixing was then carried out with 1% osmium tetroxide containing 0.8% potassium ferricyanide for 1 hour at 4° C. The tissues were then dehydrated in alcohols and were slowly included in epoxy resin (Spurr). The samples were cut and oriented correctly in the block, allowing them to polymerize for 48 hours at 60° C. They were subsequently sectioned with an Ultracut E ultramicrotome (Reichert-Jung) and the sections obtained, once contrasted, were observed with Jeol JEM 1010 Transmission Electron Microscope, determining the diameter of the fibers observed with the AxioVision.AC program (Carl Zeiss Vision).

The average of the diameters of the collagen fibrils observed was 6.825 nm for the untreated tissue and 5.774 nm for H-Lys-Asp-Val-Cit-NH$_2$ and 5.791 nm for H-Lys-Asp-Ile-Cit-NH$_2$, which involves a reduction of the diameter of the collagen fibers by 15.5% for the tissue treated with H-Lys-Asp-Val-Cit-NH$_2$ and of 15.1% for that treated with H-Lys-Asp-Ile-Cit-NH$_2$.

Example 5 (Prophetic)

Preparation of a Cosmetic Composition Containing Palm-Lys-Asp-Ile-Cit-NH$_2$

The following formulation is prepared as described in the present invention:

The components of phase A are weighed in a sufficiently large reactor and the mixture is heated at 80° C. to melt the waxes. The components of Phase B are weighed in a vessel suitable for the entire content and heated at 70° C. Phase A is added to Phase B slowly and under intense stirring, and Phase C is subsequently added to the previous mixture under stirring. Once the addition has ended, it is allowed to cool with gentle stirring and when the mixture is at room temperature, an aqueous solution of Palm-Lys-Asp-Ile-Cit-NH$_2$ and lecithin is added, it is homogenized and the pH is corrected with triethanolamine if necessary.

The cream which is obtained has a pH between 6 and 7.

| INGREDIENT | % BY WEIGHT |
| --- | --- |
| PHASE A | |
| MINERAL OIL | 8.0 |
| STEARIC ACID | 2.4 |
| CETEARYL ALCOHOL | 1.6 |
| BEESWAX | 0.8 |

-continued

| INGREDIENT | % BY WEIGHT |
|---|---|
| PHASE B | |
| GLYCERIN | 2.4 |
| WATER | 63.4 |
| PHASE C | |
| CARBOMER | 0.3 |
| TRIETHANOLAMINE | 0.9 |
| PHASE D | |
| WATER | 15.0 |
| Palm-Lys-Asp-Ile-Cit-$NH_2$ (0.05%) | 5.0 |
| LECITHIN | 0.4 |

Example 6 (Prophetic)

Preparation of Liposomes Containing H-Lys-Asp-Val-Cit-$NH_2$

Dipalmitoylphosphatidylcholine (DPPC) is weighed and dissolved in chloroform. The solvent is evaporated under vacuum until obtaining a thin layer of phospholipids, and this layer is hydrated by the treatment at 55° C. with an aqueous solution containing the peptide at the desired concentration (containing Phenonip®), obtaining the MLV liposomes. The ULV liposomes are obtained by submersing the MLV liposomes in an ultrasound bath at 55° C. for 8 cycles of 2 minutes at 5-minute intervals.

| INGREDIENT | % BY WEIGHT |
|---|---|
| DIPALMITOYLPHOSPHATIDYLCHOLINE | 4.0 |
| H-Lys-Asp-Val-Cit-$NH_2$ | 0.2 |
| PHENONIP ® | 0.5 |
| WATER | q.s. 100 |

According to a first aspect, the present invention relates to a peptide of general formula (I):

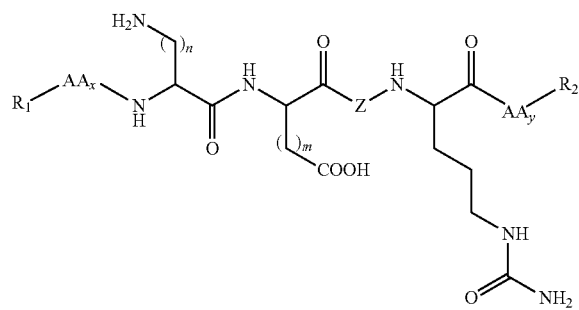

stereoisomers thereof, cosmetically and dermopharmaceutically acceptable salts thereof and mixtures thereof, wherein:
Z is selected from the group consisting of alanyl, allo-isoleucyl, glycyl, isoleucyl, isoseryl, isovalyl, leucyl, norleucyl, norvalyl, prolyl, seryl, threonyl, allo-threonyl or valyl;
n and m may vary independently from one another between 1 and 5;
AA is selected from the group consisting of natural amino acids encoded in their L- or D-form and non-encoded amino acids;
x and y may vary independently from one another between 0 and 2;
$R_1$ is selected from the group consisting of H or alkyl, aryl, aralkyl or acyl group; and
$R_2$ is selected from the group consisting of amino, hydroxyl or thiol, substituted or non-substituted with aliphatic or cyclic groups.

According to an important second aspect, in the peptide of general formula (I) $R_1$ is preferably H or linear, branched or cyclic, saturated or unsaturated $C_2$ to $C_{24}$ acyl.

According to an important aspect of the invention, in the peptide of general formula (I) $R_2$ is preferably amino or hydroxyl, substituted or non-substituted with linear, branched or cyclic, saturated or unsaturated $C_1$ to $C_{24}$ aliphatic groups.

According to an important aspect of the invention, in the peptide of general formula (I) Z is preferably L-isoleucyl, L-threonyl or L-valyl.

According to an important aspect of the invention, in the peptide of general formula (I) Z is preferably L-isoleucyl, n is 4, m is 1, $R_1$ is H or acetyl or palmitoyl and $R_2$ is amino or hydroxyl, substituted or non-substituted with methyl or ethyl or hexyl or dodecyl or hexadecyl groups.

According to an important aspect of the invention, in the peptide of general formula (I) Z is preferably L-threonyl, n is 4, m is 1, $R_1$ is H or acetyl or palmitoyl and $R_2$ is amino or hydroxyl, substituted or non-substituted with methyl or ethyl or hexyl or dodecyl or hexadecyl groups.

According to an important aspect of the invention, in the peptide of general formula (I) Z is preferably L-valyl, n is 4, m is 1, $R_1$ is H or acetyl or palmitoyl and $R_2$ is amino or hydroxyl, substituted or non-substituted with methyl or ethyl or hexyl or dodecyl or hexadecyl groups.

According to an important aspect of the invention, in the peptide of general formula (I) Z is preferably L-isoleucyl, n is 4, m is 1, x and y are 0, $R_1$ is H or acetyl or palmitoyl and $R_2$ is amino or hydroxyl, substituted or non-substituted with methyl or ethyl or hexyl or dodecyl or hexadecyl groups.

According to an important aspect of the invention, in the peptide of general formula (I) Z is preferably L-threonyl, n is 4, m is 1, x and y are 0, $R_1$ is H or acetyl or palmitoyl and $R_2$ is amino or hydroxyl, substituted or non-substituted with methyl or ethyl or hexyl or dodecyl or hexadecyl groups.

According to an important aspect of the invention, in the peptide of general formula (I) Z is preferably L-valyl, n is 4, m is 1, x and y are 0, $R_1$ is H or acetyl or palmitoyl and $R_2$ is amino or hydroxyl, substituted or non-substituted with methyl or ethyl or hexyl or dodecyl or hexadecyl groups.

According to another important aspect, the present invention relates to a process for obtaining a peptide of general formula (I) which is based on solid-phase peptide synthesis.

According to another important aspect, the present invention relates to a process for obtaining a peptide of general formula (I) which uses protective groups selected from the group consisting of Fmoc/tButyl, Fmoc/trityl and Fmoc/allyl.

According to another important aspect, the present invention relates to a cosmetic or dermopharmaceutical composition comprising a cosmetically or dermopharmaceutically effective amount of at least one peptide of formula (I) and at least one cosmetically or dermopharmaceutically acceptable excipient or adjuvant.

According to another important aspect, the present invention relates to a cosmetic or dermopharmaceutical composition comprising at least one peptide of general formula (I) incorporated into a cosmetically or dermopharmaceutically acceptable sustained release system and/or delivery system selected from the group consisting of liposomes, millicapsules, microcapsules, nanocapsules, sponges, vesicles, micellae, millispheres, microspheres, nanospheres, lipospheres, milliparticles, microparticles and nanoparticles.

According to another important aspect, the present invention relates to a cosmetic or dermopharmaceutical composition comprising at least one peptide of general formula (I) adsorbed on a solid organic polymer or mineral support selected from the group consisting of talc, bentonite, silica, starch and maltodextrin.

According to another important aspect, the present invention relates to a cosmetic or dermopharmaceutical composition in which the peptide of general formula (I) is presented in a formulation selected from the group consisting of creams, emulsions of oil and silicone in water, emulsions of oil in water, emulsions of silicone in water, emulsions of water in oil and silicone, emulsions of water in oil, emulsions of water in silicone, oils, milks, balms, foams, lotions, gels, liniments, serums, soaps, unguents, mousses, ointments, bars, pencils and sprays.

According to another important aspect, the present invention relates to a cosmetic or dermopharmaceutical composition in which the peptide of general formula (I) is incorporated into solid supports selected from the group consisting of wet wipes, hydrogels, adhesive patches, non-adhesive patches and face masks.

According to another important aspect, the present invention relates to a cosmetic or dermopharmaceutical composition in which the peptide of general formula (I) is incorporated into fabrics selected from the group consisting of bandages, girdles, pantyhose, socks, panties, brassieres and bands for arms and forearms.

According to another important aspect, the present invention relates to a cosmetic or dermopharmaceutical composition containing a peptide of general formula (I) incorporated in make-up line products selected from the group consisting of concealers, make-up foundations, make-up removal milks or lotions, eye shadows and lipsticks.

According to another important aspect, the present invention relates to a cosmetic or dermopharmaceutical composition containing a peptide of general formula (I) at a concentration between 0.000001% (by weight) and 20% (by weight).

According to another important aspect, the present invention relates to the use of a peptide of formula (I) in the preparation of a cosmetic or dermopharmaceutical composition for the treatment of the skin.

According to another important aspect, the present invention relates to the use of a peptide of formula (I) in the preparation of a cosmetic or dermopharmaceutical composition for the treatment of the skin for the purpose of reducing, delaying and/or preventing aging signs.

According to another important aspect, the present invention relates to the use of a peptide of formula (I) in the preparation of a cosmetic or dermopharmaceutical composition for the treatment of the skin of the thighs, abdomen, buttocks, chest, forearms, neck and face.

According to another important aspect, the present invention relates to the use of a peptide of formula (I) in the preparation of a cosmetic or dermopharmaceutical composition for the treatment of the skin for the purpose of softening the appearance of scars.

According to another important aspect, the present invention relates to the use of a peptide of formula (I) in the preparation of a cosmetic or dermopharmaceutical composition for the treatment of the skin of those body areas having scars.

The invention claimed is:

1. A peptide of general formula (I):

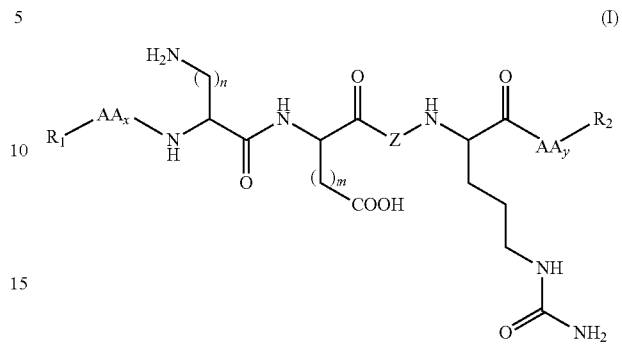

stereoisomers thereof, mixtures thereof, and cosmetically and dermopharmaceutically acceptable salts thereof, wherein:

Z is selected from the group consisting of alanyl, allo-isoleucyl, glycyl, isoleucyl, isoseryl, isovalyl, leucyl, norleucyl, norvalyl, prolyl, seryl, threonyl, allo-threonyl or valyl;

n and m range independently from one another between 1 and 5;

AA is selected from the group consisting of natural encoded amino acids in their L- or D-form and non-encoded amino acids;

x and y range independently from one another between 0 and 2;

$R_1$ is selected from the group consisting of H or alkyl, aryl, aralkyl or acyl group; and $R_2$ is selected from the group consisting of amino, hydroxyl and thiol, substituted or non-substituted with aliphatic or cyclic groups.

2. The peptide of claim 1, wherein $R_1$ is H or linear, branched or cyclic, saturated or unsaturated $C_2$ to $C_{24}$ acyl.

3. The peptide of claim 1, wherein $R_2$ is amino or hydroxyl, substituted or non-substituted with linear, branched or cyclic, saturated or unsaturated $C_1$ to $C_{24}$ aliphatic groups.

4. The peptide of claim 1, wherein Z is L-isoleucyl, L-threonyl or L-valyl.

5. The peptide of claim 1, wherein Z is L-Ile, $R_1$ is H, acetyl or palmitoyl, m is 1, n is 4 and $R_2$ is amino or hydroxyl, substituted or non-substituted with methyl or ethyl or hexyl or dodecyl or hexadecyl groups.

6. The peptide of claim 5, wherein x and y are 0.

7. The peptide of claim 1, wherein Z is L-Thr, $R_1$ is H, acetyl or palmitoyl, m is 1, n is 4 and $R_2$ is amino or hydroxyl, substituted or non-substituted with methyl or ethyl or hexyl or dodecyl or hexadecyl groups.

8. The peptide of claim 7, wherein x and y are 0.

9. The peptide of claim 1, wherein Z is L-Val, $R_1$ is H, acetyl or palmitoyl, m is 1, n is 4 and $R_2$ is amino or hydroxyl, substituted or non-substituted with methyl or ethyl or hexyl or dodecyl or hexadecyl groups.

10. The peptide of claim 9, wherein x and y are 0.

11. A method for obtaining the peptide of claim 1, comprising synthesizing the peptide on solid phase.

12. A cosmetic or dermopharmaceutical composition comprising a cosmetically or dermopharmaceutically effective amount of at least one peptide of claim 1, wherein the composition comprises at least one cosmetically or dermopharmaceutically acceptable excipient or adjuvant.

13. The cosmetic or dermopharmaceutical composition of claim 12, wherein the peptide is incorporated into a delivery system or into a sustained release system which is cosmetically or dermopharmaceutically acceptable selected from the group consisting of liposomes, millicapsules, microcapsules, nanocapsules, sponges, vesicles, micellae, millispheres, microspheres, nanospheres, liposheres, milliparticles, microparticles and nanoparticles.

14. The cosmetic or dermopharmaceutical composition of claim 12, wherein the peptide is adsorbed on a cosmetically or dermopharmaceutically acceptable organic polymer or mineral solid support selected from the group consisting of talc, bentonite, silica, starch or maltodextrin.

15. The cosmetic or dermopharmaceutical composition claim 12, wherein the composition has a formulation selected from the group consisting of creams, emulsions of oil and silicone in water, emulsions of oil in water, emulsions of silicone in water, emulsions of water in oil and silicone, emulsions of water in oil, emulsions of water in silicone, oils, milks, balms, foams, lotions, gels, liniments, serums, soaps, unguents, mousses, ointments, bars, pencils and sprays.

16. The cosmetic or dermopharmaceutical composition of claim 12, wherein the peptide is incorporated into solid supports selected from the group consisting of wet wipes, hydrogels, adhesive patches, non-adhesive patches and face masks.

17. The cosmetic or dermopharmaceutical composition of claim 12, wherein the peptide is incorporated into make-up line products selected from the group consisting of concealers, make-up foundations, make-up removal lotions, make-up removal milks, eye shadows and lipsticks.

18. The cosmetic or dermopharmaceutical composition of claim 12, wherein the peptide is incorporated into fabrics.

19. A cosmetic or dermopharmaceutical composition comprising a cosmetically or dermopharmaceutically effective amount of at least one peptide of claim 1, wherein the composition comprises an additional cosmetically or dermopharmaceutically effective amount of an active agent selected from the group consisting of an exfoliating agent, a moisturizing agent, a depigmenting or whitening agent, a pro-pigmentation agent, an anti-stretch mark agent, an anti-wrinkle agent, an antioxidant agent, an anti-glycation agent, an NO-synthase inhibitor, an anti-aging agent, an agent capable of reducing or eliminating bags under the eyes, an agent stimulating the synthesis of dermal or epidermal macromolecules and/or for preventing their degradation, an agent stimulating keratinocyte proliferation, an agent stimulating fibroblast proliferation, an agent stimulating fibroblast and keratinocyte proliferation, an agent stimulating keratinocyte differentiation, an agent that improves the dermal-epidermal junction, a dermorelaxant agent, a refirming agent, an anti-atmospheric pollution and/or anti-free radical agent, an agent acting on capillary circulation and/or microcirculation, a calming agent, an anti-inflammatory agent, an anti-microbial agent, an agent acting on cell metabolism, vitamins, an organic or mineral photoprotective agent that is active against ultraviolet A and/or B rays, and mixtures thereof.

20. A method for treating the skin comprising applying to a subject in need thereof a cosmetic or dermopharmaceutical composition comprising the peptide of claim 1.

21. A method of treatment of a skin condition requiring regulation of fibrillogenesis in a subject in need of such treatment comprising applying to said subject a cosmetic or dermopharmaceutical composition comprising the peptide of claim 1.

22. A method for reducing or delaying aging signs comprising applying to a subject in need thereof a cosmetic or dermopharmaceutical composition comprising the peptide of claim 1.

23. A method of treatment of a skin area having scars in a subject in need of such treatment comprising applying to said subject a cosmetic or dermopharmaceutical composition comprising the peptide of claim 1.

* * * * *